United States Patent [19]

Gumprecht

[11] Patent Number: 4,851,595

[45] Date of Patent: Jul. 25, 1989

[54] LIQUID PHASE HALOGEN EXCHANGE PROCESS FOR THE MANUFACTURE OF 1,1,1,2-TETRAFLUOROETHANE

[75] Inventor: William H. Gumprecht, Wilmington, Del.

[73] Assignee: E. I. Du Pont de Nemours and Company, Wilmington, Del.

[21] Appl. No.: 267,706

[22] Filed: Nov. 3, 1988

Related U.S. Application Data

[63] Continuation of Ser. No. 70,827, Jul. 7, 1987, abandoned.

[51] Int. Cl.$^4$ .................... C07C 17/20; C07C 19/02
[52] U.S. Cl. .................................................... 570/170
[58] Field of Search ........................................ 570/170

[56] References Cited

U.S. PATENT DOCUMENTS

| | | | |
|---|---|---|---|
| 1,978,840 | 10/1934 | Henne | 570/170 |
| 2,230,925 | 2/1941 | Benning | 570/170 |
| 2,431,969 | 12/1947 | Strove | 570/170 |
| 2,549,988 | 4/1951 | Perkins | 570/170 |
| 2,569,644 | 10/1951 | Stilmar | 570/170 |
| 3,201,483 | 8/1965 | Davis | 570/170 |
| 3,240,826 | 3/1966 | Davis | 260/653.8 |
| 3,287,424 | 11/1966 | Pacini et al. | 260/651 |
| 3,644,545 | 2/1972 | Buckman | 260/653.7 |
| 4,129,603 | 12/1978 | Bell | 260/653 |
| 4,311,863 | 1/1982 | Gumprecht | 570/170 |

FOREIGN PATENT DOCUMENTS 705927 3/1965 Canada .
589167 6/1947 United Kingdom .
1585938 3/1981 United Kingdom .

OTHER PUBLICATIONS

Hudlicky, "Chemistry of Organic Fluorine Compounds", MacMillan Co., N.Y. (1962), p. 93.
Sheppard et al., "Organic Fluorine Chemistry", W. A. Benjamin, Inc., N.Y. (1969), pp. 76–77.

Primary Examiner—J. E. Evans

[57] ABSTRACT

A process is disclosed for the manufacture of 1,1,1,2-tetrafluoroethane, FC-134a, more particularly for its manufacture from 1,1,1-trifluoro-2-chloroethane, FC-133a, by reaction with a high fluoride content antimony pentahalide.

11 Claims, No Drawings

LIQUID PHASE HALOGEN EXCHANGE PROCESS FOR THE MANUFACTURE OF 1,1,1,2-TETRAFLUOROETHANE

This application is a continuation-in-part, continuation of application Ser. No. 07/070,827 filed July 7, 1987, now abandoned.

BACKGROUND OF THE INVENTION

This invention relates to a process for the manufacture of 1,1,1,2-tetrafluoroethane, FC-134a, more particularly to its manufacture from 1,1,1-trifluoro-2-chloroethane, FC-133a, by reaction with a high fluoride content antimony pentahalide under surprisingly mild reaction conditions.

FC-134a, a known compound, has a low ozone depletion potential, and is potentially useful as an environmentally acceptable propellant and refrigerant.

DESCRIPTION OF THE PRIOR ART

The prior art has long recognized the resistance of the chloromethyl group, —$CH_2Cl$, to halogen exchange. Hudlicky in *Chemistry of Organic Fluorine Compounds*, MacMillan Co., New York, NY (1962), page 93, Pacini et al. in U.S. Pat. No. 3,287,424 (1966) and Buckman in U.S. Pat. No. 3,644,545 (1972) speak to the difficulty of converting —$CH_2Cl$ to —$CH_2F$ under various reaction conditions. Similarly, Sheppard and Sharts in *Organic Fluorine Chemistry*. W. A. Benjamin, Inc., NY (1969), pages 76–77, teach —$CH_2Cl$ is extremely difficult to attack and only rarely gives —$CH_2F$, also that the presence of fluorine on a neighboring carbon reduces the reactivity of a chlorine, citing the lower activity of —$CF_2CCl_3$ vs. —$CH_2CCl_3$.

This pronounced difficulty in replacing Cl by F in —$CH_2Cl$ compounds is reflected in the many halogen exchange processes the art has disclosed for converting FC-133a to FC-134a. One widely studied route, exemplified by Bell in U.S. Pat. No. 4,129,603 (1978), involves reaction of FC-133a with HF in the gas phase at high temperatures (300°–400° C.) over a solid trivalent chromium catalyst composition. The Bell and the like processes suffer major drawbacks in that they require high investment for gas phase facilities, entail stringent reaction conditions and produce gas streams having relatively low FC-134a contents due to an unfavorable equilibrium in the presence of by-product HCl. Further, as disclosed in the Bell patent, the product stream from the catalyzed high temperature reaction may also contain some 1,1-difluoro-2-chloroethylene, a troublesome impurity which is difficult to separate from FC-134a by distillation.

Gumprecht in U.S. Pat. No. 4,311,863 (1982) describes a process for converting FC-133a or the related 1,1,1-trifluoro-2-bromoethane to FC-134a by reaction with an aqueous alkali metal fluoride at 200°–300° C. under autogenous pressure. Although this process can provide FC-134a in high yields it suffers from rather stringent reaction conditions and is quite corrosive to ordinary materials of construction.

Antimony pentachloride with HF and antimony pentafluorochlorides are well known halogen exchange reagents and catalysts for preparing various fluorinated materials, including FC-133a, the starting material of the present invention, from a suitable underfluorinated chloroethane or chloroethylene. Representative such processes for the preparation of FC-133a are described in Whalley, Bristish Patent No. 589,167 (1947), involving reaction of $CF_2ClCH_2Cl$ at 144° C. with $SbF_3Cl_2$ complexed with 2 mols of HF; Ferstandig in U.S. Pat. No. 4,078,007 (1978) employing a mixed Sb(III)-Sb(V) chlorofluoride composition as catalyst for reaction of $CCl_3CH_2Cl$ with HF at temperatures up to 85° C.; Mitschke et al. in British Patent No. 1,585,938 (1981) employing $SbCl_5$ in combination with a transition metal halide as catalyst for reaction of trichloroethylene with HF at about 120°–130° C. This patent states that no tetrafluoroethane is formed. In fact, none of these references discloses that any tetrafluoroethane is formed along with FC-133a.

Antimony pentafluoride, $SbF_5$, has been utilized in the art for halogen exchange. Benning in U.S. Pat. No. 2,490,764 (1949) prepares highly fluorinated compounds $ACF_2(CF_2)_nCF_3$, where n=at least 1 and A is H, Cl or F, by reaction of $SbF_5$ with $ACF_2(CF_2)_nCF_2B$, where A and n are as above and B is Cl or F, at 175°–350° C., until at least one of A and B is replaced by F. The patent states (at column 6, lines 60–63) that, on the other hand, when $CF_3CF_2Cl$ was treated in the same manner there was little or no conversion to a completely fluorinated compound. Such marked unreactivity of the —$CF_2Cl$ in this compound undoubtedly reflects the deactivating effect of the adjacent $CF_3$ group.

Other related references are: Davis U.S. Pat. No. 3,240,826 (1966), which utilizes $SbF_4Cl$, prepared by reaction of $SbF_5$ with $SbCl_5$, to replace Br with F in $CF_3CBr_3$, $CF_2BrCHBr_2$ and $CF_3CHBr_2$ at 35°–120° C.; and Davis Canadian Patent 705,927 (1965), which employs $SbF_5$ mixed with sufficient bromine to maintain $SbF_5$ and salts thereof in liquid suspension for halogen exchange of fluorobromo compounds such as $CF_3CHBr_2$ and $CF_2BrCHBr_2$ at 20°–70° C. None of the starting materials of the Davis patents is a chloromethyl compound and none of the reaction products is FC-134a.

SUMMARY OF THE INVENTION

A process for preparing $CF_3CH_2F$ which comprises
(i) contacting $CF_3CH_2Cl$ with a liquid $SbF_{5-x}Cl_x$ composition, where x=0 to 2, at an effective temperature in the range of about 40° C. to about 175° C. to form a reaction mixture;
(ii) maintaining said contacting and temperature until at least a portion of the $CF_3CH_2Cl$ has been converted to $CF_3CH_2F$; and
(iii) recovering $CF_3CH_2F$ from the reaction mixture.

The invention process represents the first utilization of an Sb pentahalide halogen exchange agent for the preparation of $CF_3CH_2F$. It also represents the first liquid phase process for the preparation of $CF_3CH_2F$ at relatively low temperatures. Moreover, it provides $CF_3CH_2F$ in high yields at good conversions and essentially uncontaminated by 1,1,-difluoro-2-chloroethylene or other impurities difficult to separate from $CF_3CH_2F$ by ordinary distillation. Thus, $CF_3CH_2F$ (b.p. −26.5° C.) is readily recovered in a high degree of purity by simple means, such as fractional distillation. Unreacted $CF_3CH_2Cl$ (b.p. 6.1° C.) is likewise recoverable in a high degree of purity and can be directly recycled for further production of $CF_3CH_2F$ by the invention process.

That $CF_3CH_2Cl$ can be smoothly and cleanly converted to $CF_3CH_2F$ under the mild reaction conditions of the invention is surprising in view of the referenced teachings of the halogen exchange art as to the difficulty of converting —CH$_2$Cl to —CH$_2$F and the strongly deactivating effect of an adjacent CF$_3$group on halogen exchange.

DETAILED DESCRIPTION OF THE INVENTION

The invention involves contacting 1,1,1-trifluoro-2-chloroethane (CF$_3$CH$_2$Cl, b.p. 6.1° C.) with a liquid phase Sb pentahalide as defined at a temperature effective to produce 1,1,1,2-tetrafluoroethane (CF$_3$CH$_2$F, b.p. −26.5° C.). Contact between the normally gaseous CF$_3$CH$_2$Cl and the Sb pentahalide can be achieved through agitation, as by stirring, shaking or sparging gaseous reactant into the liquid phase. Alternatively, liquefied CF$_3$CH$_2$Cl can be mixed with the Sb pentahalide phase.

Pressure is not critical for the instant process. However, the reaction is conveniently and preferably conducted under pressure at least sufficient to maintain at least a portion of the CF$_3$CH$_2$Cl in the liquid state so as to promote mixing and reaction with the Sb pentahalide. Reaction pressures effective to liquefy at least a portion of the CF$_3$CH$_2$Cl are readily achieved by employing a sealed reactor or one equipped with a controllable pressure relief valve so as to enable removal of gaseous material, e.g., CF$_3$CH$_2$F and unreacted CF$_3$CH$_2$Cl as necessary or desired. Alternatively, a reflux column can be used to separate the product and return the unreacted FC-133a to the reaction zone.

In the reaction that occurs, Cl of the —CH$_2$Cl group is replaced by F of the Sb pentahalide reactant illustrated with SbF$_5$ in the following equation:

$$CF_3CH_2Cl + SbF_5 \rightarrow CF_3CH_2F + SbF_4Cl$$

Similar equations can be written for the use of other Sb pentahalide reactants of the invention, the F content of the starting Sb pentahalide being reduced by one and its Cl content increased by one for every Cl replaced by F.

The SbF$_{5-x}$Cl$_x$ reactant includes the well-known compositions SbF$_5$, SbF$_4$Cl and SbF$_3$Cl$_2$, defined by x=0, 1 and 2, respectively, and mixtures thereof. It also includes related compositions defined by fractional values of x between 0 and 2 for which no simple structural formula can be drawn but which can likewise be prepared by known processes, including the reaction of HF with SbCl$_5$, or reaction of SbF$_5$ with SbCl$_5$, or reaction of SbCl$_3$ with F$_2$ or SbF$_3$ with ClF or Cl$_2$, in the stoichiometrically required proportions.

There are two main Sb pentahalide embodiments: The first encompasses low chloridecontent compositions defined by x=less than 1.0, preferably 0.8 or less, more preferably 0.5 or less, and most preferably zero, corresponding to SbF$_5$. The other is characterized by values of x ranging from 1 to 2, i.e., SbF$_4$Cl, SbF$_3$Cl$_2$ and intermediate compositions including mixtures of SbF$_4$Cl and SbF$_3$Cl$_2$. Low chloride Sb pentahalides are preferred because of their greater halogen exchange activities and the superior results they provide.

The proportions of FC-133a and Sb pentahalide are not critical; either may be in excess over stoichiometric, if desired. Sufficient amounts of the Sb pentahalide will ordinarily be used, however, to provide at least one F for every Cl to be replaced. Since both the F content and the reactivity of the Sb pentahalide decrease during the reaction, it will usually be beneficial to maintain an excess of high fluoride-content pentahalide throughout the course of the reaction. Excess SbF$_5$, which is normally liquid, also provides for a more fluid reaction mass, thereby promoting the halogen exchange reaction through good mixing of the reactants under agitation, resulting in higher conversions of the organic component and fewer side-products.

Fluid, more easily agitated reaction mixtures may also be provided by employing a liquid diluent inert to the reactants under the reaction conditions, such as perfluorocyclohexane, H(CF$_2$)$_6$F, F(CF$_2$)$_7$F and the like highly fluorinated alkanes disclosed in Benning U.S. Pat. No. 2,490,764.

The reaction can be initiated by heating the reaction mixture under agitation at an effective temperature, which is preferbly in the 60 to 125° C. range, most preferably 70° to 100° C. While lower temperatures, e.g., 50° C. and lower, may be used, they tend to result in lower reaction rates, while higher temperatures, i.e., above 125° C., cause side reactions to increase as discussed further below. The higher the F content of the antimony pentahalide, the lower the temperature may be.

It will be noted that HF is not needed as halogen exchange reagent. However, if HF is present it will preferably be held to proportions less than one mol per mol of the Sb pentahalide since larger proportions tend to retard the conversion of CF$_3$CH$_2$Cl to CF$_3$CH$_2$F; most preferably HF will be substantially absent since its presence also increases the corrosiveness of the reaction mass. Even so, the reaction mixtures may be corrosive to various materials of construction. Preferred materials are perfluorinated polymers such as polytetrafluoroethylene, stainless steels, aluminum, platinum, aluminum-magnesium alloys, and nickel and its alloys.

The process may be conducted batchwise in a closed or ventable system. It may also be conducted in a continuos manner with the product taken off intermittently or continuously. Since CF$_3$CH$_2$F (b.p. −26.5° C.) is more volatile than CF$_3$CH$_2$Cl (b.p. 6.1° C.), it is convenient to bleed off a portion of the vapor phase intermittently or continuously through a pressure-control valve. This may be done while feeding CF$_3$CH$_2$Cl to the reaction mass intermittently or continuously. Alternatively, gaseous CF$_3$CH$_2$Cl can be fed continuously through a liquid body of the Sb pentahalide, at atmospheric or super atomspheric pressure, maintained at a suitable reaction temperature, and the gaseous product stream containing CF$_3$CH$_2$F removed therefrom continuously. In another continuous embodiment separate streams of CF$_3$CH$_2$Cl and liquid Sb pentahalide composition can be passed through a tubular reactor held at suitable reaction temperatures, the reactants being fed co-currently or counter-currently to one another, and the product stream receovered therefrom.

The normally gaseous mixture exiting the reactor stream that contains the FC-134a, unreacted CF$_3$CH$_2$Cl, if any, and by-products, if any, can be worked up in the usual ways, conveniently by first being passed through aqueous caustic to remove any acid or other water-soluble product that may be present, dried, condensed and fractionally distilled to recover the FC-134a. Unreacted CF$_2$CH$_2$Cl can be recycled to the reactor for production of additional quantities of the FC-134a.

Depending primarily on the Sb pentahalide and the reaction temperature employed, the product mixture may also contain one or more other products, such as CF$_4$, CH$_2$CF$_2$H, CF$_3$CF$_2$Cl, CF$_3$CHClF, CF$_3$CFCl$_2$, $CF_3CHCl_2$ and $CF_3CCl_3$ arising from such side reactions as carbon-carbon cleavage, chlorination and subsequent F for Cl exchange involving the chlorinated intermediate by-products. Unsaturated by-products, notably 1,1-difluoro-2-chloroethylene, are substantially absent. In general, the lower the chloro content of the Sb pentahalide reactant, the higher the Sb pentahalide/$CF_3CH_2Cl$ mol ratio and the lower the reaction temperature, the fewer are the products of carbon-carbon cleavage, the fewer are the chlorinated and over-fluorinated by-products and the smaller are their quantities. The formation of trivalent antimony resulting from replacement of hydrogen by chlorine from the $SbF_{5-x}Cl_x$ is less at the lower temperatures and at lower values of x. $SbF_5$, especially at high $SbF_5/CF_3CH_2Cl$ mol ratios and preferred reaction temperatures yields the fewest by-products and in the lowest amounts.

$CF_3CH_2Cl$ itself will normally be used as the organic reactant in the invention process. It may sometimes be advantageous, however, to produce it in situ from a suitable underfluorinated precursor. Suitable precursors are tetrahaloethanes, $C_2H_2Y_4$, where Y is Cl or F with at least two of Y being Cl. Examples are 1,1,1,2-tetrachloroethane ($CCl_3CH_2Cl$), 1,1,2,2-tetrachloroethane ($CHCl_2CHCl_2$), 1-fluoro-1,1,2-trichloroethane ($CFCl_2CH_2Cl$), 1-fluoro-1,2,2-trichloroethane ($CHFClCHCl_2$), 1,1-difluoro-2,2-dichloroethane ($CHF_2CHCl_2$), 1,1-difluoro-1,2-dichloroethane ($CF_2ClCH_2Cl$), and mixtures thereof. The antimony pentahalide quantity used will be at least sufficient to convert the underfluorinated precursor to $CF_3CH_2Cl$ and this in turn to $CF_3CH_2F$. Also, since the precursors liberate Cl during their conversion to $CF_3CH_2Cl$, the antimony pentahalide should initially be sufficiently high in F content to result in an intermediate reaction mixture containing not only $CF_3CH_2Cl$ but a "spent" antimony pentahalide, $SbF_{5-x}Cl_x$, where x has a value of 2 or less. Alternatively, or where x is greater than 2 in the residual Sb pentahalide, additional $SbF_5$ or other high fluoride-content antimony pentahalide can be added to the intermediate reaction mixture containing the in situ produced $CF_3CH_2Cl$ to bring the F content of the antimony pentahalide composition to the desired x =2 or less level for the conversion of $CF_3CH_2Cl$ to $CF_3CH_2F$ in accordance with the process of this invention.

The reaction temperature for the in situ preparation of $CF_3CH_2Cl$ can vary widely from a low of about 10° C. to as high as about 150° C. depending on the particular antimony pentahalide employed. The higher the F content of the pentahalide the lower the temperature may be. With $SbF_5$, the example, temperatures below 100° C. are suitable. In general, the temperature can be lower for the conversion of precursor to FC-133a than for the conversion of FC-133a to FC-134a because of the greater reactivity of the underfluorinated compounds.

The use of a precursor to generate FC-133a in situ is illustrated below with 1,1,1,2-tetrachloroethane and a typical antimony pentahalide of the invention:

(a) 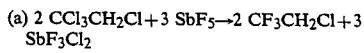 $2 CCl_3CH_2Cl + 3 SbF_5 \rightarrow 2 CF_3CH_2Cl + 3 SbF_3Cl_2$

As shown in the accompanying Examples, $SbF_3Cl_2$, i.e., the antimony pentahalide product of reaction (a), is capable of converting $CF_3CH_2Cl$ to $CF_3CH_2F$ so that this conversion may be carried out without isolation of the intermediate $CF_3CH_2Cl$. Preferably, however, the "spent" antimony pentahalide, $SbF_{5-x}Cl_x$, remaining in the reaction mixture along with the in situ produced $CF_3CH_2Cl$. will have an F content greater than 4, i.e., x will be less than 1.0

If necessary or desired, additional $SbF_5$ may be added to the $CCl_3CH_2Cl$-antimony pentahalide reaction mixture, either during the reaction or after it is completed, in order to increase the overall F content of the antimony pentahalide and thereby facilitate the conversion of the in situ-produced $CF_3CH_2Cl$ to the desired $CF_3CH_2F$ end product.

The same technique for increasing the fluorinating potential of the reaction mixture containing the in situ-produced $CF_3CH_2Cl$ can also be used when the initial reaction with the precursor involves a relatively low F-content antimony pentahalide, e.g., $SbF_3Cl_2$, as shown by equation (b).

(b) 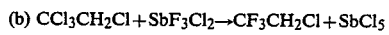 $CCl_3CH_2Cl + SbF_3Cl_2 \rightarrow CF_3CH_2Cl + SbCl_5$ $SbCl_5$ is incapable of converting $CF_3CH_2Cl$ to $CF_3CH_2F$. however, the addition of $SbF_5$ in amounts of 1.5 mols or more, preferably 4 mols or more per mol of the $SbCl_5$ produced, will increase the F content of the "spent" antimony pentahalide enough to convert $CF_3CH_2Cl$ to $CF_3CH_2F$ in the process of the invention.

Similar conversions to $CF_3CH_2Cl$ and then to $CF_3CH_2F$ can be achieved through reaction of any of the other precursors disclosed above with any of the high F-content antimony pentahalides of this invention provided the intermediate reaction mixture has a sufficiently high F content to convert the in situ-produced $CF_3CH_2Cl$ to $CF_3CH_2F$ under the conditions of the invention process.

It will be noted that 1,1,2,2-tetrachloroethane will likewise yield $CF_3CH_2Cl$, via intermediately formed $CF_2HCCl_2$ which rearranges during the reaction to the unsymmetrical isomer ($CF_2ClCH_2Cl$), ultimately forming $CF_3CH_2Cl$.

In the following examples, all percentages are weight percentages, unless otherwise indicated.

EXAMPLE 1

A mixture of 118.5 g. (1 mol) of FC-133a and 434 g. (2 mols) of antimony pentafluoride ($SbF_5$) was heated and shaken in a Hastelloy C bomb at 100° C. for 3 hours. During this time the internal pressure increased from 105 to 145 psig. The bomb at 75° C. was vented through 10% aqueous KOH, and the volatiles were collected in a Dry Ice-cooled trap. A total of 60 g. was collected in the trap. The composition of this material by gas chromatography was 30.3% FC-134a, 7.5% 1,1,1,2-tetrafluoro-2-chloroethane (FC-124), 61.5% FC-133a, 0.3% pentafluoroethane (FC-125) and possibly 0.3% of tetrachloroethylene. The recovery antimony compounds contained 2.04% Sb(III) and 49.65 Sb(V).

EXAMPLE 2

Similar to Example 1, 118.5 g. (1 mol) of FC-133a and 217 g. (1 mol) of $SbF_5$ were heated at 125° C. for 3 hours. A total of 105 g. of volatiles was collected in the trap from the scrubbing system. This material analyzed as 30.9% FC-134a, 5.8% FC-124, 53.7% FC-133a and 9.4% FC-125.

EXAMPLE 3

In a 150 ml. s.s. cylindrical pressure vessel containing a polytetrafluoroethylene-coated magnetic stirring bar was placed 65.5 g. (0.30 mol) of SbF$_5$ under a blanket of dry nitrogen in a dry box. A valve was attached. The system was pressure-tested with nitrogen to 500 psig to ensure against subsequent leakage, cooled in a Dry Ice-methanol bath and evacuated. An inverted gas cylinder containing liquefied FC-133a (99.896 area % by gas chromatography) was attached to the system by way of a short piece of 1/2" s.s. tubing having a volume of about 25 ml. The tubing was evacuated and then filled with liquid FC-133a (under pressure) from the reservoir. The FC-133a trapped in the tubing was then drawn into the cold, evacuated cylinder containing the SbF$_5$. This charging procedure was repeated until 109.2 g. (0.92 mol) of FC-133a had been added.

The cylinder, with its valve closed, containing the SbF$_5$ and FC-133a was placed in a hot oil bath and heated to 80°–90° C., with magnetic stirring of its contents, and held overnight. A vapor sample was withdrawn through the valve, scrubbed through dilute aqueous KOH solution to remove any acids present and analyzed by gas chromatography. The sample was found to contain about 19% (area) FC-134a, and two other components (not identified) in the amounts of 2.6% and 0.3% in addition to unreacted FC-133a. The identities of FC-134a and FC-133a were determined by "spiking" the sample with known samples of these materials and by mass spectroscopy.

For the chromatography, a 6 m. column was used containing "Krytox" perfluorinated polyether supported on Carbopak B, and packed in 1/8" s.s. tubing; the carrier gas was N$_2$ at a flow of 50cc per minute.

EXAMPLES 4–7

The same type of equipment and procedure was used as in Example 3. When mixtures of SbF$_5$ and antimony pentachloride (SbCl$_5$ - also charged under dry nitrogen in a dry box) were used to generate SbF$_{5-x}$Cl$_x$, they were heated without venting to about 100° C. and mixed to equilibrate before adding the FC-133a. The conditions and results are as follows:

| Example | SbF$_5$ grams | SbF$_5$ mols | FC-133a grams | FC-133a mols |
|---|---|---|---|---|
| 4* | 174.2 | 0.80 | 94.8 | 0.80 |

| Temperature/Time | Volatile Components Identity | Area % |
|---|---|---|
| 80–90° C./overnight | CF$_4$(FC-14) | 0.051 |
| | FC-125 | 3.729 |
| | FC-134a | 50.154 |
| | CF$_3$CF$_2$Cl (FC-115) | 0.104 |
| | FC-124 | 4.610 |
| | FC-133a | 41.311 |
| | | 99.959 |

*The recovered antimony compounds contained: 1.27% Sb(III), 44.4% Sb(V) and about 40% F$^-$.

| Example | SbF$_5$ grams | SbF$_5$ mols | SbCl$_5$ grams | SbCl$_5$ mols | FC-133a grams | FC-133a mols |
|---|---|---|---|---|---|---|
| 5 | 111.7 | 0.515 | 38.5 | 0.128 | 55.7 | 0.47 |

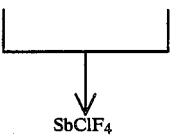

↓

SbClF$_4$

| Temperature Time | Volatile Components Identity | Area % |
|---|---|---|
| 80–88° C./overnight | FC-14 | 0.214 |
| | FC-125 | 0.090 |
| | FC-134a | 3.389 |
| | FC-115 | 0.149 |
| | FC-124 | 7.522 |
| | FC-133a | 88.366 |
| | CF$_3$CFCl$_2$ (FC-114a) | 0.150 |
| | CF$_3$CHCl$_2$ (FC-123) | 0.099 |
| | | 99.979 |

| Example | SbF$_5$ grams | SbF$_5$ mols | SbCl$_5$ grams | SbCl$_5$ mols | FC-133a grams | FC-133a mols |
|---|---|---|---|---|---|---|
| 6 | 151.1 | 0.697 | 131.0 | 0.438 | 25.7 | 0.22 |

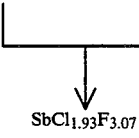

↓

SbCl$_{1.93}$F$_{3.07}$

| Temperature Time | Volatile Components Identity | Area % |
|---|---|---|
| 85–90° C./overnight | FC-14 or CH$_2$F$_2$ (FC-32) | 0.286 |
| | FC-134a | 0.053 |
| | FC-115 | 0.038 |
| | FC-124 | 0.894 |
| | FC-133a | 93.520 |
| | FC-114a | 2.548 |
| | FC-123 | 2.342 |
| | CF$_3$CCl$_3$ (FC-113a) | 0.064 |
| | | 99.745 |
| 105–110° C./14 hrs. | FC-14, -32 | 0.613 |
| | FC-125 | 0.038 |
| | FC-134a | 0.144 |
| | FC-115 | 0.630 |
| | FC-124 | 6.560 |
| | FC-133a | 64.568 |
| | FC-114a | 10.429 |
| | FC-123 | 15.831 |
| | FC-113a | 0.296 |
| | | 99.109 |

| Example | SbF$_5$ grams | SbF$_5$ mols | FC-133a grams | FC-133a mols |
|---|---|---|---|---|
| 7 | 273.5 | 1.262 | 54.4 | 0.46 |

| Temperature/Time | Volatile Components Identity | Area % |
|---|---|---|
| About 100° C./overnight | FC-14 | 0.051 |
| | FC-125 | 8.378 |
| | FC-134a | 43.582 |
| | FC-115 | 0.015 |
| | FC-124 | 6.121 |
| | FC-133a | 41.781 |
| | | 99.929 |

EXAMPLE 8

A Hastelloy C bomb of the type used in Examples 1 and 2 was evacuated, and 252 g. (1.16 mols) of $SbF_5$ was sucked in from a reservoir cylinder which was warmed with a heat gun to facilitate transfer. The bomb was then cooled in Dry Ice, and about 100 g. (5.0 mols) of anhydrous HF was sucked in, followed by 108 g. (0.91 mol) of FC-133a.

The bomb was shaken and heated at 80°–84° C. overnight. It was then cooled in Dry Ice, and any HCl pressure was vented. The bomb was warmed in a 60° C. water bath, and the volatiles were vented into a Dry Ice-cooled s.s. gas cylinder. A total of 112 g. was collected in the cylinder. Examination of the Hastelloy bomb after the experiment showed significant corrosive attack had occurred.

The collected volatiles were scrubbed through dilute aqueous KOH solution and analyzed as before by gas chromatography. The mixture contained 0.124% (area) FC-134a and 99.699% FC-133a.

EXAMPLES 9 and 10

The same type of equipment and procedure was used as in Example 3. The conditions and results are tabulated as follows:

| Example | SbF_5 grams | SbF_5 mols | FC-133a grams | FC-133a mols |
|---|---|---|---|---|
| 9 | 224.0 | 1.033 | 89.1 | 0.75 |

| Temperature/Time | Volatile Components Identity | Area % |
|---|---|---|
| 40–43° C./ overnight | FC-14, −32 | 0.029 |
| | FC-125 | 0.002 |
| | FC-134a | 2.172 |
| | FC-115 | 0.025 |
| | FC-124 | 0.047 |
| | FC-133a | 97.663 |
| | FC-114a | 0.036 |
| | FC-123 | 0.020 |
| | | 99.994 |

| Example | SbF_5 grams | SbF_5 mols | FC-133a grams | FC-133a mols |
|---|---|---|---|---|
| 10 | — | 1.03 | 86 | 0.73 |
| (SbCl_{0.017}F_{4.983} recovered from Example 9) | | | | |

| Temperature/Time | Volatile Components Identity | Area % |
|---|---|---|
| 170–175° C./ overnight | FC-14, −32 | 0.042 |
| | FC-125 | 22.306 |
| | FC-134a | 7.609 |
| | FC-115 | 0.583 |
| | FC-124 | 15.171 |
| | FC-133a | 46.705 |
| | FC-114a | 0.166 |
| | FC-123 | 7.064 |
| | FC-113a | 0.050 |
| | | 99.696 |

EXAMPLE 11

The procedure used in Example 3 was used to react 249 g. (1.149 mols) of $SbF_5$ with 38.4 g. (0.229 mol) of 1,1,1,2-tetrachloroethane at 85°–90° C. overnight. Gas chromatographic analysis of the volatiles after scrubbing showed that FC-133a, 82.258%, and FC-134a, 1.786%, were produced along with other products.

We claim:

1. A process for preparing $CF_3CH_2F$ which comprises
   contacting $CF_3CH_2Cl$ with a liquid $SbF_{5-x}Cl_x$ composition, where x=0 to 2, at an effective temperature in the range of about 40° C. to about 175° C. to form a reaction mixture, said liquid $SbF_{5-x}Cl_x$ composition present for contacting with the $CF_3CH_2Cl$ in a stoichiometric quantity sufficient to provide at least one F for every Cl of said $CF_3CH_2Cl$ to be replaced;
   maintaining said contacting and temperature until at least a portion of the $CF_3CH_2Cl$ has been converted to $CF_3CH_2F$; and
   recovering $CF_3CH_2F$ from the reaction mixture.

2. The process of claim 1 wherein the liquid $SbF_{5-x}Cl_x$ is characterized by x=less than 1.

3. The process of claim 2 wherein the liquid $SbF_{5-x}Cl_x$ is characterized by x=0.

4. The process of claim 1 wherein the liquid $SbF_{5-x}Cl_x$ is characterized by X=1 to 2.

5. The process of claim 4 wherein the liquid $SbF_{5-x}Cl_x$ is characterized by x=a fractional number between 1 and 2, including mixtures of $SbF_4Cl$ and $SbF_3Cl_2$.

6. The process of claim 1 wherein the temperature is about 60° C. to about 125° C.

7. The process of claim 1 wherein the temperature is about 70° C. to about 100° C.

8. The process of claim 1 wherein the contacting and maintaining steps occur in the presence of less than a molar proportion of HF based on the Sb compound.

9. The process of claim 1 wherein the contacting and maintaining steps occur in the in the substantial absence of HF.

10. The process of claim 1 further including the step of forming $CF_3CH_2Cl$ in situ from a suitable underfluorinated precursor, $C_2H_2Y_4$, where Y=Cl or F, with at least two of Y being Cl.

11. The process of claim 10 wherein the underfluorinated precursor is selected from the group consisting of 1,1,1,2-tetrachlorethane ($CCl_2CH_2Cl$), 1,1,2,2-tetrachloroethane ($CHCl_2CHCL_2$), 1-fluoro-1,1,2-trichloroethane ($CFCl_2CH_2Cl$), 1-fluoro-1,2,2-trichloroethane ($CHFClCHCl_2$), 1,1-difluoro-2,2-dichloroethane ($CHF_2CHCl_2$), 1,1-difluoro-1,2-dichloroethane ($CF_2ClCH_2Cl$), and mixtures thereof.

* * * * *